United States Patent
LaPrade et al.

(10) Patent No.: US 11,452,521 B2
(45) Date of Patent: Sep. 27, 2022

(54) ANGLED SUTURE PASSER AND METHOD OF USE THEREOF

(71) Applicant: Smith & Nephew, Inc., Memphis, TN (US)

(72) Inventors: Robert F. LaPrade, Avon, CO (US); David R. Diduch, Charlottesville, VA (US); David Kent Gregoire, Mission Viejo, CA (US); Jeffrey Wyman, Naples, FL (US); George William White, Corona, CA (US); Carmel Ilka Bijoux, Swampscott, MA (US); Jennifer Ng, Quincy, MA (US)

(73) Assignee: Smith & Nephew, Inc., Memphis, TN (US)

( * ) Notice: Subject to any disclaimer, the term of this patent is extended or adjusted under 35 U.S.C. 154(b) by 581 days.

(21) Appl. No.: 15/939,934

(22) Filed: Mar. 29, 2018

(65) Prior Publication Data
US 2018/0280018 A1    Oct. 4, 2018

Related U.S. Application Data

(60) Provisional application No. 62/478,204, filed on Mar. 29, 2017.

(51) Int. Cl.
*A61B 17/04* (2006.01)
*A61B 17/06* (2006.01)
(Continued)

(52) U.S. Cl.
CPC ........ *A61B 17/0491* (2013.01); *A61B 17/062* (2013.01); *A61B 17/06066* (2013.01);
(Continued)

(58) Field of Classification Search
CPC .............. A61B 17/0491; A61B 17/062; A61B 17/06066; A61B 17/282;
(Continued)

(56) References Cited

U.S. PATENT DOCUMENTS

| | | | | |
|---|---|---|---|---|
| 6,235,057 B1 * | 5/2001 | Roger | ................ | A61B 17/1675 606/304 |
| 7,232,447 B2 * | 6/2007 | Gellman | ............ | A61B 17/0469 606/144 |

(Continued)

FOREIGN PATENT DOCUMENTS

EP    2939604    11/2015

OTHER PUBLICATIONS

Invitation to Pay Additional Fees for PCT/US2018/025138 dated Aug. 14, 2018, 17 pages.
(Continued)

*Primary Examiner* — Julian W Woo
(74) *Attorney, Agent, or Firm* — Norman F. Hainer, Jr.

(57) ABSTRACT

A suture passer which is sized and shaped to be inserted through the femoral notch during a meniscal repair. The suture passer includes upper and lower jaws that may be straight or that may have an angled offset in relation to the common axis of the suture passer in order to gain an indirect access to meniscal tissue in a constricted space. The jaws of the suture passer may be angled, either to the left or to the right, up to 45 degrees from the central axis of the shaft. The suture passer is also able to grasp meniscal tissue prior to suture passing. A nitinol needle housed within one of the jaws can then be deployed to pass a preloaded suture through the tissue to be captured on the opposite side of the tissue.

22 Claims, 3 Drawing Sheets

(51) Int. Cl.
*A61B 17/28* (2006.01)
*A61B 17/062* (2006.01)
*A61B 17/00* (2006.01)

(52) U.S. Cl.
CPC ........ *A61B 17/282* (2013.01); *A61B 17/0469* (2013.01); *A61B 2017/00738* (2013.01); *A61B 2017/00862* (2013.01); *A61B 2017/00867* (2013.01); *A61B 2017/0609* (2013.01); *A61B 2017/06042* (2013.01); *A61B 2017/06095* (2013.01)

(58) Field of Classification Search
CPC .. A61B 2017/00738; A61B 2017/0609; A61B 2017/06042; A61B 2017/06095; A61B 17/0469; A61B 2017/00867; A61B 2017/00862
See application file for complete search history.

(56) References Cited

U.S. PATENT DOCUMENTS

| | | | |
|---|---|---|---|
| 7,842,050 B2 | 11/2010 | Diduch et al. | |
| 8,623,032 B2 | 1/2014 | Diduch et al. | |
| 9,011,454 B2 | 4/2015 | Hendrickson et al. | |
| 9,211,118 B2 | 12/2015 | Gregoire et al. | |
| 9,393,009 B2 | 7/2016 | Diduch et al. | |
| 9,439,647 B1 | 9/2016 | Bourland, III et al. | |
| 9,700,299 B2* | 7/2017 | Saliman .............. | A61B 17/0469 |
| 2002/0147456 A1 | 10/2002 | Diduch et al. | |
| 2003/0105474 A1* | 6/2003 | Bonutti .............. | A61B 17/0401 |
| | | | 606/139 |
| 2007/0225737 A1* | 9/2007 | Messerly ............. | A61B 17/064 |
| | | | 606/151 |
| 2008/0269783 A1* | 10/2008 | Griffith .............. | A61B 17/0469 |
| | | | 606/144 |
| 2009/0131956 A1 | 5/2009 | Dewey et al. | |
| 2012/0283754 A1* | 11/2012 | Murillo .............. | A61B 17/0469 |
| | | | 606/145 |
| 2015/0313589 A1 | 11/2015 | Hendrickson | |
| 2016/0367243 A1* | 12/2016 | Martin ............. | A61B 17/06133 |

OTHER PUBLICATIONS

EP Office Action for Patent Application No. 18718993.1 dated Sep. 2, 2020, 7 pages.
Japanese Application No. 2019-548304—Notice of Reasons for Rejection—dated Feb. 14, 2022.

* cited by examiner

ANGLED SUTURE PASSER AND METHOD OF USE THEREOF

CROSS-REFERENCE TO RELATED APPLICATIONS

This application is a non-provisional of U.S. Provisional Application No. 62/478,204 filed Mar. 29, 2017, entitled "ANGLED SUTURE PASSER AND METHOD OF USE THEREOF", the full disclosure of which is incorporated herein by reference.

FIELD

The present disclosure concerns surgical instruments for manipulating suture. In particular, the present disclosure relates to an instrument for passing suture through tissue.

BACKGROUND

In many surgical procedures, such as anterior cruciate ligament (ACL) surgeries of the knee or shoulder instability repairs, suture is used to close wounds and may be used to repair damage to ligaments and soft tissue. As part of the repair, suture may be routed through tissues to stitch or hold the tissue together, or for the purposes of capturing the tissue and anchoring it to a surgical implant, such as a suture anchor. Known instruments for suture passing typically consist of a piercing portion or needle, which may be curved, and a means for retaining the suture within a portion of the needle to enable the suture to be manipulated and passed through tissue during the repair procedure.

During ACL surgeries, it has been noted that as high as 50% of patients have a coincident injury to the meniscus. The meniscus is a C-shaped piece of fibrocartilage which is located at the peripheral aspect of the knee joint between the condyles of the femur and the tibia on the lateral and medial sides of the knee. A meniscal injury is often a tear at the posterior root where the meniscus attaches to the tibia. Recent advances in surgical instruments have permitted doctors to repair, rather than remove, the torn tissue. However, the anatomy of the knee, in combination with standard arthroscopic ACL portal placement, limits access to the posterior root attachment of the meniscus.

In current approaches to meniscal repair, direct arthroscopic access from the anterior side to the posterior root of the meniscus passes directly under the femoral condyle. The space between the femoral condyle and the tibial plateau is extremely small and also curved, since the two mating anatomies are convex/concave. Thus, optimal suture passers for direct access would need to be 2 mm or less in width, and therefore potentially of insufficient strength to perform suture passing. Alternatively, an indirect path that would provide greater access space passes the instrument through the femoral notch formed between the femoral condyles. However, this approach would require an angled suture passer to place the suture in the proper location. Additionally, since the meniscal root may be loosely held, it is desirable for the suture passer to be able to grasp meniscal tissue prior to suture passing. Generally since many portions of the human anatomy include small curved spaces, providing a means to use an indirect path through these spaces to grasp and pass a suture through tissue may be used in a variety of procedures, such as the capsule and labrum for shoulder instability, and procedures in the hip joints, for example.

SUMMARY

Disclosed herein is a suture passer which is sized and shaped to be inserted through a curved space within the body, such as, but not limited to the femoral notch during a meniscal repair. The suture passer may include upper and lower jaws that may be straight or that may have an angled offset in relation to the common axis of the suture passer in order to gain an indirect access to meniscal tissue. The angled offset may improve access to the posterior root via the femoral notch. The jaws of the suture passer may be angled, either to the left or to the right, up to 45 degrees from the central axis of the shaft. The suture passer is also able to grasp tissue such as the meniscus or posterior root thereof, prior to suture passing. A nitinol needle may be housed within one of the jaws that can then be deployed to pass a preloaded suture through the tissue. Thus, the suture passer of this disclosure provides easier access to meniscal tissue within a confined space of the knee joint because the angled jaws are able to reach at least partially around structures like the femoral condyle. Furthermore, the suture passer of this disclosure may be used to access tissue in a confined and potentially curved space within a joint in other procedures, such as a shoulder joint during a shoulder instability repair, labral or rotator cuff repair; such as capsular closure during hip procedures, or other knee repairs such as meniscal radial tear repair to potentially treat meniscal extrusion. Further examples of the angled suture passer and methods of use thereof of this disclosure may include one or more of the following, in any suitable combination.

In examples, the angled suture passer includes a shaft having a proximal end, a distal end, and a longitudinal axis extending therebetween. A lumen extends through the shaft along the longitudinal axis. A tissue penetrating member is positioned substantially within and slidable through the lumen of the shaft. The tissue penetrating member includes a distal portion having super-elastic properties and further includes a transverse opening for selectively carrying a suture. A first jaw member and a second jaw member are connected to the shaft. The first jaw member is moveable relative to the second jaw member and has an opening configured for passage of the distal portion of the tissue penetrating member. The second jaw member houses at least a portion of the tissue penetrating member. A puncturing projection is formed at the distal-most end of the tissue penetrating member and slidable through the second jaw member. The puncturing projection is movable between a first position, in which the distal portion of the tissue penetrating member is in a substantially stressed configuration and substantially contained within the lumen of the shaft, and a second position, in which the distal portion of the tissue penetrating member is in a substantially curved, unstressed configuration and extendable distally through and beyond the opening in the first jaw member such that the transverse opening of the tissue penetrating member carrying the strand of suture is positioned completely outside of the first jaw member and the second jaw member. In examples, the first jaw member and the second jaw member are angularly or curvedly offset relative to the longitudinal axis of the shaft.

In further examples, the suture passer includes a handle to manipulate movement of the first jaw member and the second jaw member. The transverse opening of the tissue penetrating member comprises a hook. The tissue penetrating member is either substantially non-hollow or substantially hollow. The second jaw member includes a transverse channel for pre-loading the device with the suture. The distal portion of the tissue penetrating member is made of Nitinol. The first jaw member includes a suture capture member disposed within the opening of the first jaw member for capture of the suture. The suture capture member has an elongate aperture formed by edges on each opposed side. The edges define a suture capture surface configured for passage of the needle and the suture. In examples, the angle of the offset of the first jaw member and the second jaw member relative to the longitudinal axis of the shaft is between about 0 degrees and about 45 degrees, and preferably between 10-25 degrees or stated otherwise, the lateral offset of the first jaw member and second jaw member distal tip may be between 1-8 mm, and preferably between 2-5 mm from the longitudinal axis of the shaft. Generally speaking, this angle or lateral offset may be any non-zero value that improves target tissue access through a curved space, given the procedure and patient anatomy. A cross-section of the tissue penetrating member is substantially circular. In the second position, the tissue penetrating member defines at least one curve along a first plane parallel to a longitudinal axis of the device shaft having a first radius of curvature greater than or equal to 3 times a thickness of the tissue penetrating member, while in the first position, the tissue penetrating member defines at least one curve along the first plane having a second radius of curvature selected to be larger than the first radius of curvature.

In examples, a method of passing suture through tissue of this disclosure includes: 1) positioning a suture passing device described above or near tissue at a location in a human body; actuating the first jaw member to position the tissue between the first jaw member and the second jaw member and grasping said tissue therebetween; 2) extending the tissue penetrating member such that the suture is captured by the transverse opening; and 3) further extending the tissue penetrating member to penetrate the tissue and to form a passage for the suture. The tissue penetrating member thus passes the suture through the tissue at a location offset from a longitudinal axis of a shaft of the suture passing device. Further examples of the method include passing the device through a cannula and/or preloading the device with the suture.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
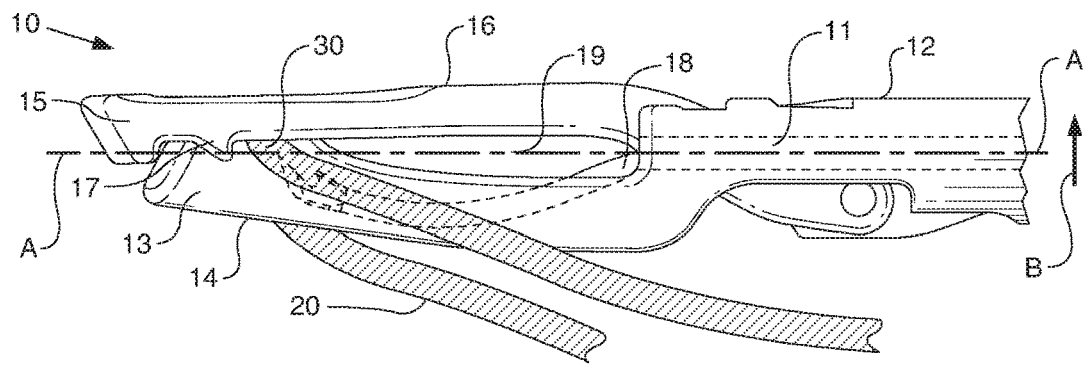
FIG. 1A illustrates a side view of an exemplary angled suture passer of this disclosure with the jaws in a closed position.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1A, there is shown a side view of an exemplary suture passer 10 of this disclosure, wherein a first plane is defined as parallel to the longitudinal axis A and parallel to the view shown such that the direction B is parallel to the first plane. A second plane, is also defined and relied upon in later discussion that is also parallel to the longitudinal axis, and perpendicular to the first plane, and best shown in FIG. 1C. The suture passer 10 has an elongate, shaft 12 extending from a handle (not shown). A lumen 11 extends through the shaft 12. A distal end of the shaft 12 may curve downward to terminate in a distally-extending lower jaw 14. Alternatively, lower jaw 14 may be a separate element (not shown), coupled to and extending distally from a distal end of the shaft 12, and may be coupled so as to be a fixedly attached, stationary jaw. Lower jaw 14 may define a downward curve at the proximal end so as to define an opening or gap 19 at the proximal end of the jaw between the two facing surfaces of the lower and upper jaw (14 and 16 respectively). This may give clearance for tissue disposed therein and allow distal end to be closer together. Lower jaw 14 may comprise an elongate body with an elongate channel 40 disposed therein, and as shown in FIG. 1A, the jaw defines a first curve along the first plane, curving initially away from longitudinal axis at the proximal end, curving back towards and across the longitudinal axis at the tip or distal end 13. This first curve along the first plane aids to keep the distal tips of the two jaws (14 and 16) closer together and also aids in reducing stresses by allowing some curvature on a needle 18 retained within the elongate channel (shown in dotted lines on FIG. 1A) and described later. This first curve also aids in directing said needle 18 (described later) as it extends towards the upper jaw 16, described in more detail later. A substantially linear upper jaw 16 is attached to the shaft 12 such that the upper jaw 16 and the lower jaw 14 may be biased in the closed position, as shown. In examples, the upper jaw 16 may pivot about a longitudinal axis (A) relative to the shaft 12 (as shown) or, alternatively, the connection between lower jaw 14 and the upper jaw 16 may be a reciprocating or cam system wherein the upper jaw 16 is movable relative to lower jaw 14. A length of the upper jaw 16 is selected such that it extends distally beyond the lower jaw 14. In examples, a widest diameter of the suture passer 10 is about 8 mm, or is otherwise selected to fit down an 8 mm cannula, which typically has an inner diameter of 8.2 mm. Advantageously, the outer edges of the suture passer 10 are rounded to avoid damage to surrounding cartilage and other tissue when the suture passer 10 is used to access a confined space.

The lower jaw 14 also includes a transverse channel 30 (best seen in FIGS. 1B and 1D) for initial retention of a length of suture 20 therethrough in preparation for stitching the suture 20 through soft tissue and subsequently capturing the suture 20. A tissue receiving area 19 is defined between the lower jaw 14, the upper jaw 16, and the distal end of the shaft 12. Jaws are shaped such that area 19 is larger towards the proximal end of the jaws as a relief for tissue disposed therein, while still maintaining a smaller distance between the two jaws towards the distal ends of jaws, adjacent the channel 30 to aid in a reliable suture capture during operation. In examples, a width of the distal end 15 of the upper jaw 16 is selected to be larger than a width of the distal end 13 of the lower jaw 14, such that the lower jaw 14 is housed within opposing downwardly-extending protrusions or teeth 17 of the upper jaw 16 when the suture passer 10 is in the closed position. The location of the teeth helps to enclose and control the tissue within the jaws, while not overly compressing the tissue that the needle 18 has to penetrate through, making the action of the needle 18 more reliable. Notably, in the closed position, the teeth 17 do not block the channel 30 in the lower jaw 14 so that the suture passer 10 can be passed effectively through an arthroscopic portal when in the closed position. Teeth 17 are distally spaced from channel 30. In other examples, not shown, the width of the upper jaw 16 and the width of the lower jaw 14 may be substantially the same.

In various examples, not shown, the handle is an in-line type handle. The handle may include an opening for accommodating a user's fingers. In alternative examples, the handle does not include such an opening, and the user's fingers simply fit around the handle. The handle may also include one or more actuators to open/close the upper jaw 16 relative to the lower jaw 14 and/or to extend/retract the needle 18. For example, the actuator(s) may be in the form of a thumb activated slider which may be moved distally away from the handle to activate the suture passer 10. The actuator may be biased by suitable means, such as a spring, to default to a closed/retracted position when an application force is removed, for example, when a user removes pressure from a finger or thumb. In other examples, the handle may be a scissor-grip or pistol-grip type handle with suitable actuation members. In examples, the suture passer 10 may include two slots for opposite ends of the suture to allow passage through two parts of the meniscus in subsequent steps, creating a vertical mattress suture or circlage for vertical tears. Thus, the needle 18 could be shifted between positions within the handle to pick up the second strand of suture.

Figure 1B:
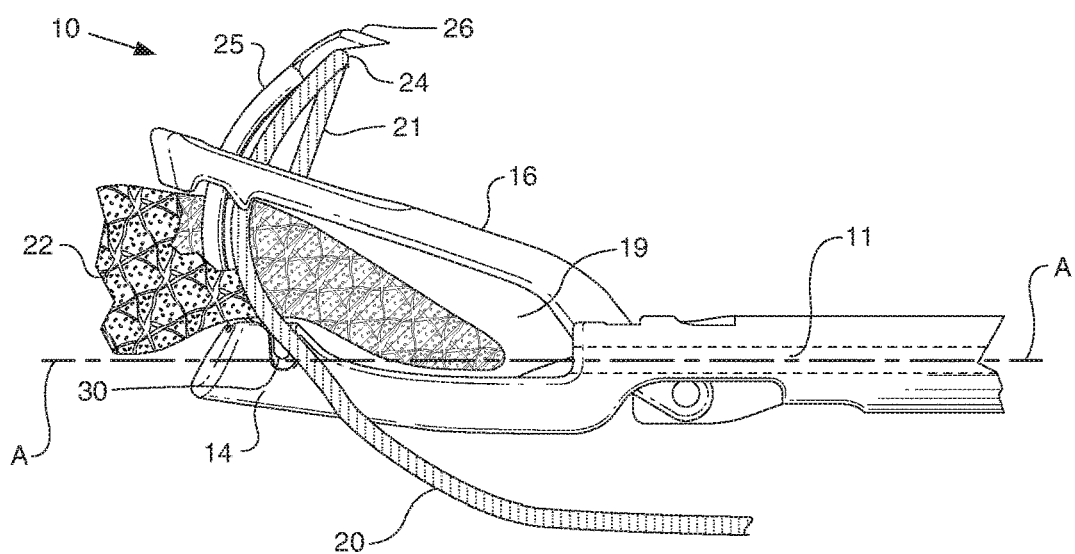
FIG. 1B illustrates the suture passer of FIG. 1A with the jaws grasping tissue and the needle extending through the tissue.

Turning now to FIG. 1B, it can be seen that a curved needle 18 for passing the suture 20 through soft tissue 22, such as meniscal tissue, is configured to be axially movable within and extendable from the lumen 11 of the shaft 12 and a channel 40 in the lower jaw 14, such that the needle tip 26 may be moved from a retracted position, wherein the needle 18 is withdrawn or shielded from the tissue receiving area 19, to an extended position, wherein the needle 18 is displaced through an opening in the upper jaw 16 and through the soft tissue 22. The needle 18 may be housed along a portion of the lower jaw 14 in the first position with the needle tip adjacent to and slightly retracted from the transverse channel 30. The lower jaw 14 may comprise a channel 40 along its length for housing and sheltering the needle 18 in the first position, the channel having a distal ramp 41 (FIG. 1D) adjacent the transverse channel 30 of the lower jaw so as to direct the needle 18 towards the transverse channel 30 to reliably pick up the length of suture 20 disposed within the transverse channel 30. Since the needle 18 is curved in its unstressed configuration (described later), which defines the needle trajectory as it extends out of the channel 40, the ramp 41 is not considered a means for significantly altering the extended trajectory of the needle, merely a local control surface to aid in reliable suture capture near channel 30. As the needle extends and is released to its preformed geometry, the needle is shown in FIG. 1B to curve approximately perpendicular to the longitudinal axis A and potentially even in a proximal direction. It follows therefore that a ramp may not be necessary and no ramp or an open distal end 13 of the lower jaw 14 may suffice. Counter to this, should the needle 18 be produced without a preformed curve as disclosed, a ramp or bumper may be required to induce a needle trajectory, which would predominantly extend linearly from the ramp and not continue to curve approximately perpendicular to the longitudinal axis A and potentially in a slight proximal direction as shown in FIG. 1B. As shown in FIG. 1B, the needle tip 26 is more proximally disposed relative to the suture channel 30. This curved trajectory keeps the needle tip 26 close to the upper jaw 16 rather than extending away from it, which helps to reduce injury that the needle tip 26 may cause tissue as it moves through and away from the upper jaw 16. Housing 40 may have a covered portion 42 to better grasp tissue and protect the needle 18 and housing 40 from the tissue. Housing 40 may be curved, along the first plane discussed earlier related to FIG. 1A so as to reduce stresses on needle 18 and improve engagement reliability with a suture capture aperture 34 of upper jaw 16. This covered portion 42 may help retains the preformed needle 18 within the housing 40.

Figure 1C:
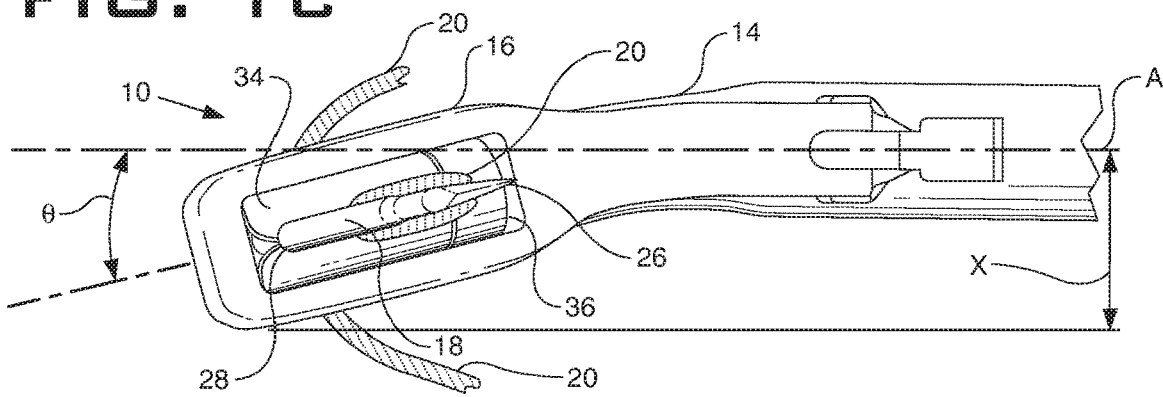
FIG. 1C illustrates a top view of the suture passer of FIG. 1B with the tissue removed.
Figure 2A:
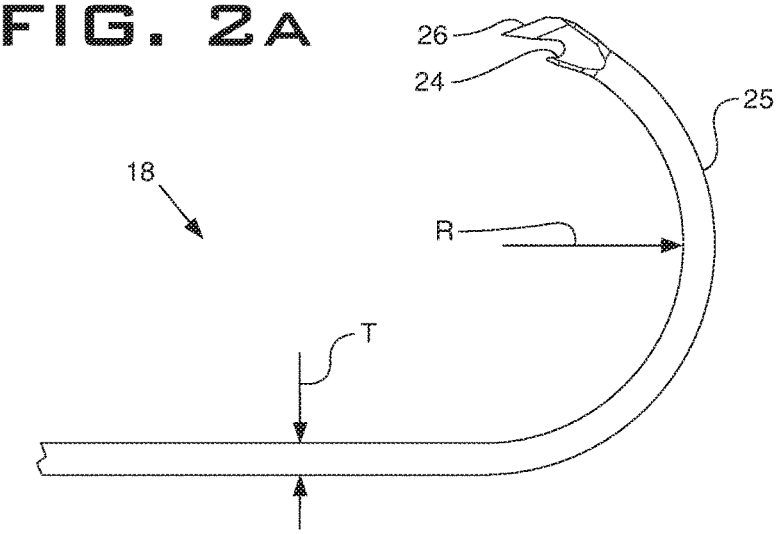
FIGS. 2A and 2B illustrate views of a needle of the angled suture passer, in accordance with the present disclosure.

In examples, at least a distal portion of the needle 18 is comprised of a super-elastic material, such as nitinol, and has a generally circular cross-section. A circular cross section provides some added lateral stiffness and helps the needle 18 retain its path as it extends through the tissue and upper jaw 16. The needle 18 may be substantially hollow or substantially non-hollow. The needle 18 may be tapered and may have a length of smaller diameter 18a or non-circular cross section adjacent the distal tip of the needle and a length of larger diameter proximally extending therefrom 18b. This may allow for easier insertion though the suture capture member 34, described below. The super-elastic nature of the material allows the needle 18 to be disposed in a generally linear configuration relative to its preformed shape while placed in the retracted position so as to be readily conform to the housing 40 within the lower jaw 14, and then return to a form closer to the preformed, curved configuration during the displacement of the needle 18 from the retracted to the extended position. The needle 18 is preformed to include a bend or curved region 25 at the distal end of the needle 18 as shown in FIG. 2A, that shows the needle 18 before assembly with the suture passer 10 in an unstressed configuration. The curved region 25 may define a preformed curve along the first plane as defined earlier, parallel to the longitudinal axis of the shaft and proximal end of the needle, the curve readily seen in FIGS. 2A and 2B. When assembled within housing or channel 40 of the lower jaw 14, which generally follows the curves of the lower jaw 14, the needle is placed in a stressed configuration whereby the needle curvature 25 is straightened along the first plane and curved along the second plane, as described earlier; the curve along the second plane inducing a laterally offset placement of the needle through tissue disposed between the jaws as seen in FIG. 1C. In alternative embodiments not shown, the needle 18 may be produced so as to have a more complex curve, or a curve preformed along both the first and second plane, so as to adjust for or compensate for the induced lateral curve (second plane) of the channel 40. For example this more complex curve may be in the opposing direction to the angular offset of the jaw so as to counter the induced curve along the second plane by the lower jaw curve. The preformed needle 18 may therefore direct the needle tip 26 in an opposing direction relative to the angle of the jaws to some degree.

Figure 1D:
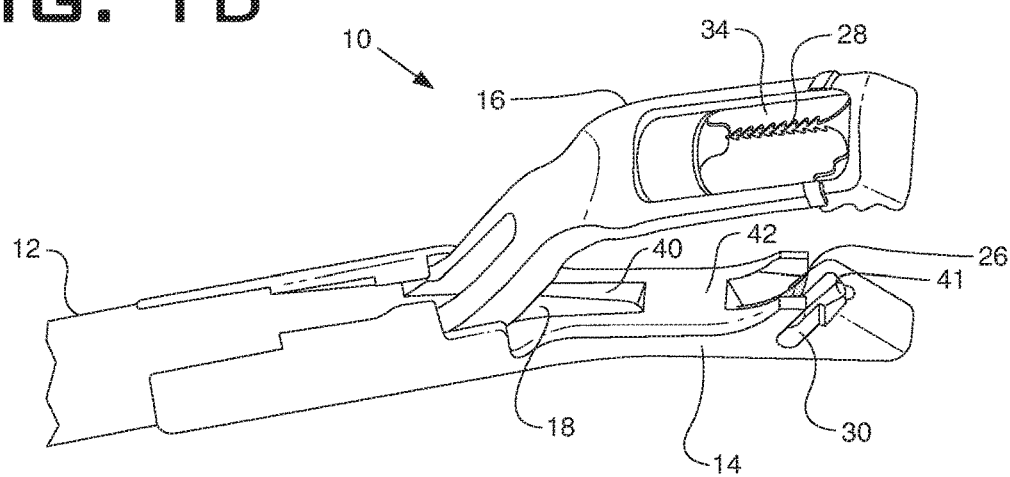
FIG. 1D illustrates an angled suture passer with the jaws in an open position and the needle in a retracted configuration.

In examples, in the extended position, the needle 18 defines at least one curve as shown in FIGS. 1B and 2A having a first radius of curvature R greater than or equal to 3 times the thickness of the needle 18 (T). Moreover, in the retracted position as shown in FIGS. 1A and 1D, the needle 18 defines at least one curve R' (not shown) having a second radius of curvature selected to be larger than the first radius of curvature. In the fully-extended position of the needle 18, the suture 20 that has been drawn through the tissue 22 forms a suture portion 21 which protrudes from and is disposed above the upper jaw 16. In examples, the suture portion 21 may form a looped configuration.

Still referring to FIG. 1B, the upper jaw 16 may be actuated by the handle to move to an open position to enable the suture passer 10 to immobilize the tissue 22 between the upper jaw 16 and the lower jaw 14. With the tissue 22 grasped between the upper jaw 16 and the lower jaw 14, the needle 18 may be deployed by actuation of the needle deployment member or trigger in the handle to the extended position. The needle 18 is advanced axially toward the distal end of the suture passer 10 such that a transverse opening 24 of the needle 18, which may be in the form of a distally facing hook, engages the suture 20 accommodated in the channel 30 the lower jaw 14. As the needle 18 is advanced in a generally distal direction, the curved region 25 of the needle 18 gradually releases towards the unstressed configuration so as to urge the needle tip 26 toward the upper jaw 16 and the needle tip 26 thereby penetrates and enters the underside of the soft tissue 22 grasped between the upper jaw 16 and the lower jaw 14. The protrusions or teeth 17 assist in retaining the tissue 22 within the tissue receiving area 19 as the needle 18 advances through the soft tissue 22. In order to aid in maintaining a reliable needle and thereby suture trajectory though the tissue, the needle cross section is preferably a circular cross section, and the target tissue is kept relatively uncompressed; compressed tissue is considered more resistant to piercing and more likely to alter the path of the needle 18 there through. This relatively uncompressed tissue is achieved by medial convex portions or cavities on the opposing faces of the lower and upper jaw providing a relief, and teeth 17 disposed around a lateral perimeter of the upper jaw to retain the tissue. FIG. 1D shows a cavity on lower jaw 14 adjacent channel 30. In examples in which a thickness of the grasped tissue 22 is about 3 mm, a length of the needle 18 is selected such that the distal portion of the needle 18 extends no more than about 3 mm to about 4 mm above the upper jaw 16, to avoid contact with surrounding tissue.

FIG. 1C illustrates the suture passer 10 of FIG. 1B in a top surface view, with the tissue removed for simplicity. In FIG. 1C, it can be seen that a suture capture member 34 is disposed within an opening 36 in the upper jaw 16, the suture capture member defining a curved flexible construct defining the medial cavity the upper jaw 16. The suture capture member 34 may be in the form of a removable cartridge or may be an integrated structural component of the upper jaw 16. A detailed description and examples of suture capture members can be found in commonly assigned U.S. Pat. No. 9,211,118, the complete disclosure of which is incorporated herein by reference. In examples, the suture capture member 34 is comprised of high-temper, spring steel material.

Figure 2B:
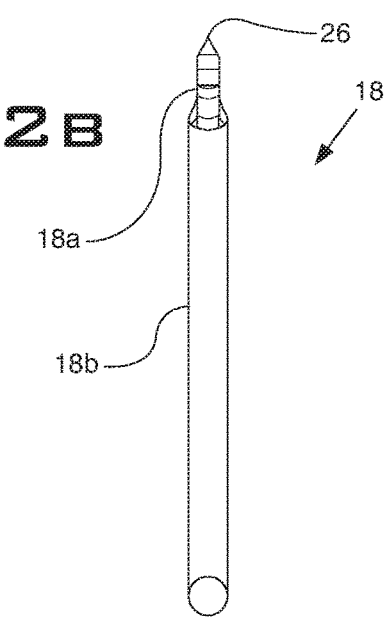

Also shown in FIG. 1C, the upper jaw 16 and the lower jaw 14 are laterally angled or curve away from the longitudinal axis (A) of the shaft 12 along the second plane. As viewed from above, the upper jaw 16 and the lower jaw 14 may be angled either to the left (as shown) or to the right, the angle Θ being up to 45 degrees from the longitudinal axis (A) of the shaft 12, and preferable between 10-25 degrees. The angle Θ is predominantly formed along a portion of the jaws 14 and 16, proximally spaced from the capture member 34, such that the more distal portion of both jaws may be straight. The angle Θ offsets the tips of the jaws from the longitudinal axis a distance X, that may range from 1-8 mm, and more preferably for an 8 mm device, 2-5 mm. For other devices that target alternative areas of the patient, larger or smaller angles and offsets are envisioned, and generally speaking, this angle and lateral offset may be any non-zero value that improves target tissue access through a curved space, given the procedure and patient anatomy. In other examples, not shown, the upper jaw 16 and the lower jaw 14 may be angled up from the longitudinal axis (A) of the shaft 12 to allow positioning of the suture passer 10 in the back of the dished, medial compartment. It is also contemplated by this disclosure that the upper jaw 16 and the lower jaw 14 may follow a radius or a spiral arc extending away from the longitudinal axis (A) along the second plane. Advantageously, the angled suture passer 10 provides the surgeon with greater access space when inserted through the femoral notch formed between the femoral condyles of the knee joint. The jaws (14, 16) are shown to follow the same angle offset (as each other so as to extend parallel relative to each other). In alternative embodiments (not shown) each jaw may have a slightly different angled offset from each other, so as to be staggered and potentially adjust for an altered path of the needle 18 as it extends through the tissue 22. The inventors have found that if the needle 18 is produced with a curve in a single plane only, as shown in FIGS. 2A and 2B, the needle 18 may exit from housing 40 biased against a lateral wall closest to the longitudinal axis A of the suture passer 10 and not central to the housing 40. Needle 18 may continue along a reliable trajectory along the longitudinal axis; however it may be laterally offset relative to a suture capture aperture 28 due to the engagement with the lateral wall. Therefore providing an upper jaw with a reduced offset may compensate for this trajectory change and improve needle engagement with suture capture member 34. For example angle Θ may be 0-5 degrees less on the lower jaw 14 than the upper jaw 16, or lower jaw 14 may be angled 17 degrees from the longitudinal axis A, while the upper jaw 16 may be angled 18 degrees from the longitudinal axis A.

Figure 3A:
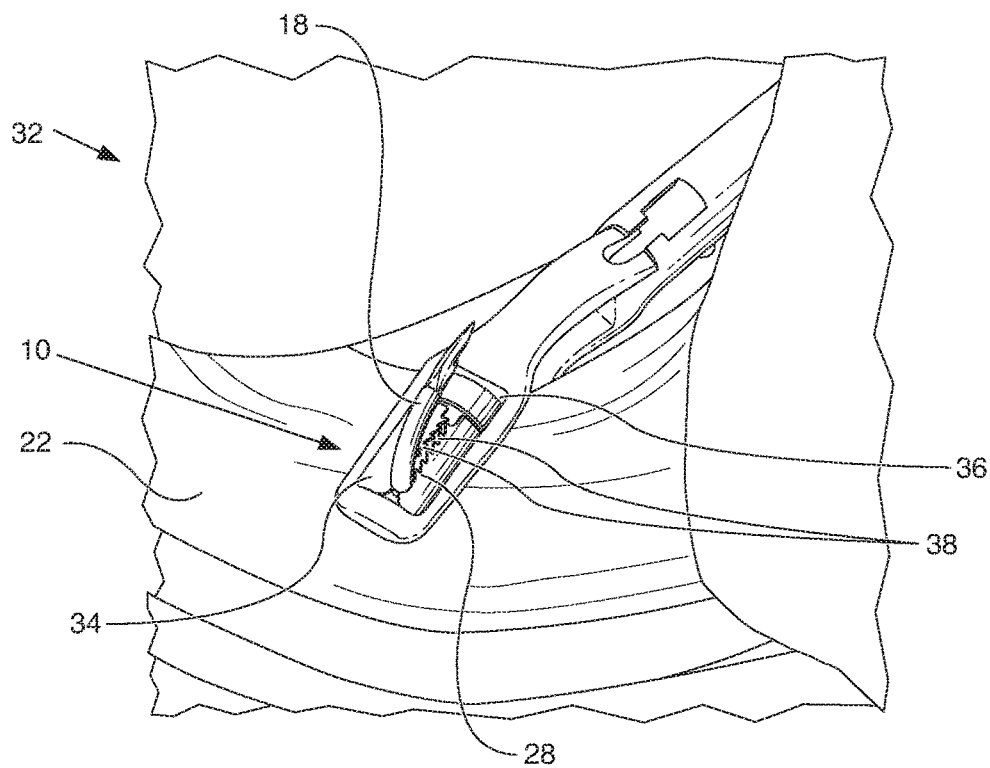
FIG. 3A illustrates a left-directed angled suture passer during a meniscal root repair.
Figure 3B:
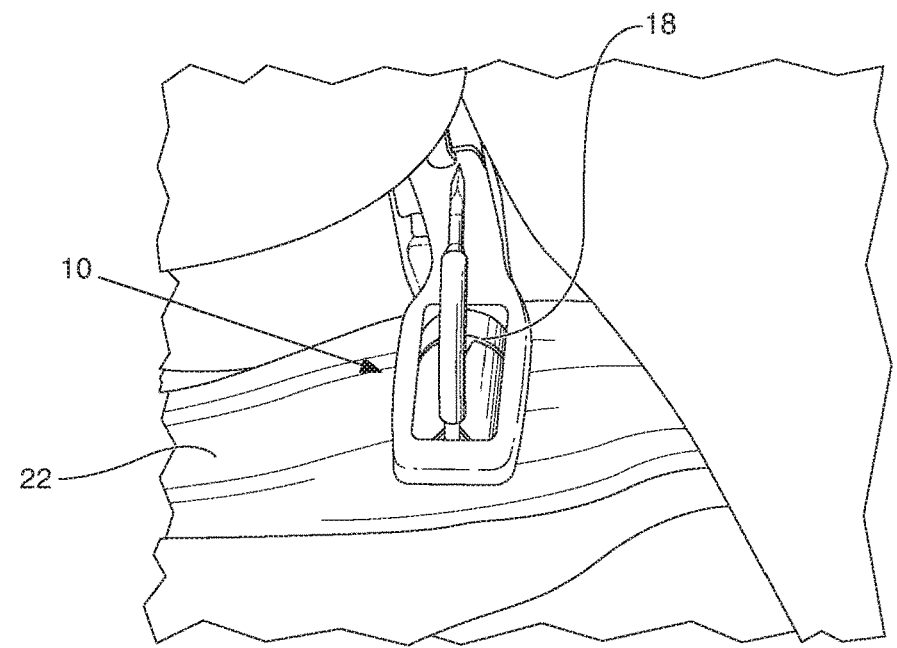
FIG. 3B illustrates a right-directed angled suture passer during a meniscal root repair.

FIGS. 3A and 3B further illustrate the angled suture passer 10 as previously described passed through the femoral notch 32 of the knee joint during a meniscal repair. For the sake of simplicity, the captured suture (20) is not shown in the drawings. FIG. 3A shows a left-directed angled suture passer 10 and FIG. 3B illustrates a right-directed angled suture passer 10. Further details of the suture capture member 34 are also illustrated in FIG. 3A. In FIG. 3A, it can be seen that the suture capture member 34 comprises an elongate aperture 28 formed by edges 38 on each opposed side. The edges 38 define a suture capture surface, which may be configured as opposed serrated edges (as shown), through which the needle 18 and a portion of the suture are passed. It is also contemplated by this disclosure that the suture capture surface may include a plurality of interdigitating teeth, a plurality of opposed notches, or other similar opposed edge features. In examples, a size of the aperture 28 is selected to be large enough that the suture capture member 34 does not restrict the movement of the needle 18 during displacement to the extended position. However, the size of the aperture 28 is also selected to be sufficiently small enough to prevent the suture 20 from passing back through the suture capture member 34. Aperture 28 is disposed along the central axis of the upper jaw, and in line or directly above an exit opening in the lower jaw 14 where the needle 18 exits. In alternative embodiments this aperture 28 may be slightly laterally offset (0-2 mm) from the exit opening (not shown) or may be angled relative to the lower jaw axis to better capture the needle 18 and suture 20, this offset or angle an alternative means to compensate for a potential path of the needle 18 given the interaction between the elastic nature of the needle 18, the performed shape of the needle and the induced needle course directed by the lower jaw housing 40 and ramp 41 and jaw curve. Returning now to FIGS. 1A-C, in operation, the user (e.g., surgeon) may insert the suture passer 10 through a cannula, not shown, to a repair site. Generally, the suture passer 10 is preloaded with a suture 20 (FIG. 1A). The suture 20 may be a shuttle suture with a suture 20 attached, or it may be a suture 20 that has already been positioned within the tissue 22. Once the suture passer 10 is near the tissue 22 to be sutured, the suture passer 10 is actuated so that the tissue 22 may be positioned between the lower jaw 14 and the upper jaw 16. This target tissue 22 may be at a location offset from the longitudinal axis of the suture passer, the distal end of the suture passer, having a curved or angled portion so as to better access this target tissue 22. Once the target tissue 22 is so positioned, the needle 18 may be at least partially actuated to capture the suture 20 on the suture capture member 24. The needle 18 may be further actuated to penetrate the tissue 22, the penetration at a location medial to the lower and upper jaws (14, 16) and laterally offset from the longitudinal axis of the suture passer 10 and form a passage for the suture 20. With the needle tip 26 and the suture 20 drawn through soft tissue 22, the actuation of the needle 18 continues until the needle 18 advances into and through the opening 36 in the upper jaw 16 (FIG. 1C). Concurrently, the needle 18 and the suture 20 are also directed through the aperture 28 of the suture capture member 34.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A suture passing device comprising:
    a shaft having a proximal end, a distal end, and a longitudinal axis extending therebetween;
    a first jaw member and a second jaw member connected to the shaft distal end, the first jaw member moveable relative to the second jaw member in a first direction and wherein a portion of the first jaw member includes a curved portion, configured to laterally offset a distal end of the first jaw member from the longitudinal axis in a second direction by a first dimension, and wherein a portion of the second jaw member includes a curved portion, configured to laterally offset a second jaw distal end from the longitudinal axis in the second direction by a second dimension, the second dimension different from the first dimension; the second direction different than the first direction;
    a tissue penetrating member positioned substantially within and slidable through the second jaw, the tissue penetrating member including a distal portion having super-elastic properties, a distal-most portion of the tissue penetrating member further including a transverse opening configured to selectively carry a suture;
    wherein the tissue penetrating member is slidable between a first and a second position, wherein in the first position the distal portion of the tissue penetrating member is in a substantially stressed configuration and the distal-most portion of the tissue penetrating member is recessed within the second jaw member and wherein in the second position the distal portion of the tissue penetrating member is in a substantially curved, unstressed configuration and extended through and beyond an opening in the first jaw member at a location laterally spaced from the longitudinal axis in the second direction.

2. The device of claim 1, further comprising a handle to manipulate movement of the first jaw member and the second jaw member.

3. The device of claim 1, wherein the transverse opening of the tissue penetrating member comprises a hook defining a curved surface that faces towards a distal end of the suture passing device.

4. The device of claim 1, wherein the second jaw member comprises a transverse channel for pre-loading the device with a length of suture.

5. The device of claim 1, wherein the distal portion of the tissue penetrating member comprises Nitinol.

6. The device of claim 1, wherein the first jaw member comprises a suture capture member disposed within the opening of the first jaw member for capture of a length of suture.

7. The device of claim 1 wherein the first jaw member distal end is laterally offset to a lesser degree than the second jaw member distal end, configured to compensate for an altered path of the tissue penetrating member through the tissue between the first jaw member and second jaw member, path a result of a bias of the tissue penetrating member interacting with the second jaw.

8. The device of claim 1, wherein the angle of the offset of the first jaw member and the second jaw member relative to the longitudinal axis of the shaft is between about 10 degrees and about 25 degrees.

9. The device of claim 1, wherein a cross-section of the tissue penetrating member is substantially circular.

10. The device of claim 1, wherein, in the second position, the tissue penetrating member defines at least one curve having a first radius of curvature greater than or equal to 3 times a thickness of the tissue penetrating member.

11. The device of claim 10, wherein, in the first position, the tissue penetrating member defines at least one curve having a second radius of curvature selected to be larger than the first radius of curvature.

12. The device of claim 1 wherein the second jaw member defines a tissue grasping surface that is concave and curves away from the longitudinal axis at a proximal end of the tissue grasping surface and curves towards the longitudinal axis at a distal end of the grasping surface.

13. The device of claim 1 wherein the first jaw member includes a proximal hinge portion and a distal suture capture portion, and a neck portion extending therebetween, and wherein the neck portion defines the curved portion.

14. The device of claim 1 wherein the second direction is perpendicular to the first direction.

15. A suture passing device comprising:
a shaft having a length and a longitudinal axis;
a first jaw member and a second jaw member extending from a distal end of the shaft, the second jaw member stationarily coupled to the shaft distal end and thereby defining a stationary jaw and the first jaw member having a suture capturing aperture and moveable relative to the second jaw member in a first direction, and wherein a distal end of both the first and second jaw members are angularly or curvedly offset in a second direction relative to a proximal end of both jaw members, the second direction different than the first direction; and
a tissue penetrating member having a puncturing tip, movable between a first position wherein the puncturing tip is recessed within the second jaw member, and a second position in which the tissue penetrating member has collected a length of suture preloaded along a channel in the second jaw member and then extended through the suture capturing aperture with the length of suture; and wherein the first jaw member is angularly or curvedly offset in the second direction less than that of the second jaw member to improve capture of the length of suture with the suture capturing aperture.

16. The suture passing device of claim 15 wherein the first and second jaws are curvedly or angularly offset so as to grasp and place the length of suture through a target tissue offset from the longitudinal axis of the device.

17. The suture passing device of claim 15 wherein the tissue penetrating member has super-elastic properties and wherein in the first position, a portion of the tissue penetrating member is in a substantially stressed configuration, and in the second position a portion of the tissue penetrating member is in a substantially curved, unstressed configuration.

18. The suture passing device of claim 15 wherein in the second position the length of suture and puncturing tip is positioned completely outside of the first jaw member and extends proximally along an outer surface of the first jaw.

19. The device of claim 15 wherein the second direction is perpendicular to the first direction.

20. A method of passing suture through a portion of meniscus while avoiding the space directly under a femoral condyle comprising:
inserting a suture passing device through the femoral notch and around the femoral condyle to indirectly access the portion of meniscus, the suture passing device comprising:
a shaft having a proximal end, a distal end, and a longitudinal axis extending therebetween, a lumen extending through the shaft along the longitudinal axis;
a tissue penetrating member positioned substantially within and slidable through the lumen of the shaft, the tissue penetrating member including a distal portion having super-elastic properties, the distal portion further including a transverse opening for carrying a suture therein;
a first jaw member and a second jaw member connected to the shaft, the first jaw member moveable relative to the second jaw member in a first direction and wherein the first jaw has an opening configured for passage of the distal portion of the tissue penetrating member therethrough, the second jaw member defining a stationary jaw and housing at least a portion of the tissue penetrating member;
a puncturing projection at the distal-most end of the tissue penetrating member and slidable through the second jaw member, the puncturing projection movable between a first position, wherein the distal portion of the tissue penetrating member is in a substantially stressed configuration and substantially contained within the lumen of the shaft, and a second position, wherein the distal portion of the tissue penetrating member is in a substantially curved, unstressed configuration and extendable distally through and beyond the opening in the first jaw member such that the transverse opening of the tissue penetrating member carrying the strand of suture is positioned completely outside of the first jaw member and the second jaw member;
wherein a distal end of both the first jaw member and the second jaw member are angularly or curvedly offset from a proximal end of both the first and second jaw members in a second direction, perpendicular to the first direction;
positioning the first and second jaw members around the femoral condyle with the shaft extending along the femoral notch and actuating the first jaw member to position the meniscus tissue between the first jaw member and the second jaw member;
extending the tissue penetrating member such that the suture is captured on the transverse opening;
further extending the tissue penetrating member to penetrate the tissue and to form a passage for the suture, whereby the tissue penetrating member passes the suture through the portion of the meniscus and me a at a location laterally offset in the second direction from the longitudinal axis of the suture passing device.

21. The method of claim 18, further comprising passing the device through a cannula.

22. The method of claim 18, further comprising preloading the device with the suture.

* * * * *